United States Patent [19]

Korbanka et al.

[11] 3,988,331

[45] Oct. 26, 1976

[54] PROCESS FOR THE MANUFACTURE OF HIGH MOLECULAR WEIGHT ALIPHATIC MONOCARBOXYLIC ACIDS

[75] Inventors: Helmut Korbanka, Adelsried; Werner Strassberger, Gersthofen, both of Germany

[73] Assignee: Hoechst Aktiengesellschaft, Frankfurt am Main, Germany

[22] Filed: Apr. 4, 1975

[21] Appl. No.: 565,007

Related U.S. Application Data

[63] Continuation of Ser. No. 318,671, Dec. 26, 1972, abandoned.

[30] Foreign Application Priority Data

Dec. 31, 1971 Germany............................ 2165858

[52] U.S. Cl.............................. 260/413; 260/533 R
[51] Int. Cl.$^2$...................... C11C 1/00; C07C 51/00

[58] Field of Search........................ 260/413, 533 R

[56] References Cited
UNITED STATES PATENTS

| | | | |
|---|---|---|---|
| 2,450,858 | 10/1948 | Fitzpatrick.......................... | 260/413 |
| 2,470,515 | 5/1949 | Myers................................ | 260/413 |
| 3,692,810 | 9/1972 | Washecheck....................... | 260/413 |

*Primary Examiner*—Winston A. Douglas
*Assistant Examiner*—John F. Niebling
*Attorney, Agent, or Firm*—Connolly and Hutz

[57] ABSTRACT

By oxidation of straight-chained alpha-olefins having 16 to 70 carbon atoms with chromosulfuric acid, the corresponding aliphatic monocarboxylic acids are prepared without noteworthy degradation. The compounds obtained are suitable, inter alia, for making waxy esters or metal soaps which can be worked up into floor polishes or lubricants for plastic materials.

2 Claims, No Drawings

PROCESS FOR THE MANUFACTURE OF HIGH MOLECULAR WEIGHT ALIPHATIC MONOCARBOXYLIC ACIDS

This application is a continuation of application Ser. No. 318,671 filed Dec. 26, 1972 and now abandoned.

The present invention relates to high molecular weight, aliphatic monocarboxylic acids and to a process for their manufacture.

Numerous syntheses have been proposed to produce high molecular weight, aliphatic carboxylic acids. However, only a few of them are used on a technical scale. Even nowadays the demand of high molecular weight fatty acids or wax acids, for example lauric acid, palmitic acid, stearic acid, behenic acid or montanic acid, is satisfied almost exclusively by natural products. To produce fatty acids on an industrial scale, fats and oils are saponified in known manner in an acid medium under pressure, however depending on the degree of purity, a subsequent distillation of the acids is required. Fatty acids of the aforesaid types can also be obtained by air oxidation of straight chained paraffin hydrocarbons. The latter process has the disadvantage that the oxidation cannot be controlled with respect to the attack of the oxygen on the hydrocarbon molecule, so that it is non-specific. The attack of the oxygen takes place over the entire molecule so that besides the desired long-chained fatty acids, low molecular weight, partly water-soluble carboxylic acids are formed to a larger extent. Moreover, a paraffin hydrocarbon air oxydation product contains, besides the carboxylic acids, considerable amounts of other oxygen-functional compounds, such as for example, esters, alcohols and ketones, which after neutralisation of the acids, must be removed by extraction from the soaps formed. As further process, which is used to a limited extent only, there is mentioned the caustic potash melt of alcohols. The drawback of this process resides in the fact that it is necessary to work at a relatively high temperatures of from 250° to 350° C with an excess of alkali and that considerable amounts of alkali metal salts are obtained as by-products when the formed carboxylic acids are isolated by the addition of mineral acids. Finally, relatively large amounts of high-molecular weight, monocarboxylic acids are obtained by the known chromosulfuric acid oxydation of optionally deresinified natural waxes, such as for example crude montan wax. This process is based on the fact that the esters present in the crude montan wax are first split hydrolytically by the sulfuric acid during the oxidative bleaching, whereupon the oxidation of the resulting alcohols takes place to yield the corresponding carboxylic acids. Another process for the production of high molecular weight carboxylic acids uses as starting materials alpha-olefins having 4 to 12 carbon atoms, which are first transformed into a mixture of olefins with inner double bond, using definite catalysts with splitting off of ethylene. By ozonolysis and oxygen oxydation these olefins are then transformed into the desired carboxylic acids (c.f. German Application laid open to public inspection DOS No. 2,047,102). Due to the fact that this process is carried out at low temperatures (5° to 10° C) and in solution and that the formed carboxylic acids are isolated from the oxydation mixture, preferably by fractional distillation, it is rather complicated and expensive.

It has now been found that high molecular weight, aliphatic monocarboxylic acids can be obtained in a much simpler manner and with very good yields by oxidation of olefins when straight-chained alpha-olefins having 16 to 70 carbon atoms in the molecule or mixtures of such alpha-olefins are oxidized with chromosulfuric acid in the molten state in aqueous phase at a temperature in the range of from 60° to 180° C.

It has been surprising and could not have been foreseen that by the working method according to the invention alpha-olefins having more than 15 carbon atoms can be transformed directly into monocarboxylic acids without difficulty and in straight manner since the chromosulfuric acid oxydation of low-molecular weight alpha-olefins does not take place in the desired sense. Alpha-olefins having up to 10 carbon atoms in the molecule, for example, are decomposed practically quantitatively under the applied reaction conditions to carbon dioxide and water.

As starting material for the chromosulfuric acid oxydation are used, as mentioned above, exclusively straight-chained olefins with terminal double bond and more than 15 carbon atoms in the molecule. There are mentioned by way of example hexadecene(1), octadecene(1), eicosene(1) and docosene(1), from which the higher aliphatic carboxylic acids of the fatty acids series having up to 21 carbon atoms are formed, whereas the carboxylic acids of the wax acid series, i.e. straight-chained monocarboxylic acids having 22 or more carbon atoms in the molecule, are obtained from alpha-olefins with longer chains having up to 70 carbon atoms, such as for example, alpha-olefin mixtures with a number of carbon atoms of 22 to 28 or 24 to 48.

It proved advantageous to use aqueous chromosulfuric acid having a sulfuric acid concentration of from 300 to 650 grams, preferably 400 to 550 grams per liter of oxidation solution. The amount of chromic acid, calculated as chromium trioxide $CrO_3$, can vary from 50 to 140 grams per liter of oxidation solution. The use of a lower concentration of $CrO_3$ is also possible, on principle, but from a technical point of view, it is disadvantageous because it necessitates larger amounts of liquid.

It is also possible to use the chromosulfuric acid in portions, preferably in such a manner that in a first stage a preoxidation is carried out with at least 50% of the total amount, then the consumed oxidation agent is separated and the oxidation is terminated with the remainder of the oxidation agent. When operating in this manner the carboxylic acid content in the oxidation product obtained is especially high.

The required minimum amount of oxidation agent calculated as $CrO_3$ depends on the molecular weight characterized by the iodine number of the alpha-olefin or alpha-olefin mixture to be oxidized. It can be determined according to the following reaction equation:

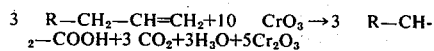

Besides the oxidation, a degradation takes place to a minor extent according to

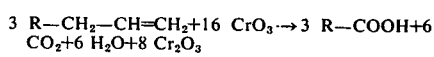

In order to obtain as quantitative as possible an oxidation reaction it is thus advantageous to use an excess of chromic acid. Hence, for 3 moles of alpha-olefin to be oxidized 10 to 40, preferably 20 to 30 moles of chromium trioxide are used.

The oxidation is performed at a temperature in the range of from 60° to 180° C, preferably 90° to 120° C, more preferably 100° to 115° C. If necessary, the reaction should be carried out in a pressure vessel, in which case the formed carbon dioxide is allowed to escape from the system over a pressure cooler.

To carry out the process of the invention the molten alpha-olefin is introduced all at once into the chromosulfuric acid heated at reaction temperature, whereupon the mixture is allowed to react while stirring. The oxidation is terminated without noticeable evolution of heat after 4 to 8 hours, which can be controlled by determination of the consumption of chromic acid. Alternatively, the molten alpha-olefin can be placed first into the reaction vessel and chromosulfuric acid added without different results being obtained.

After the stirrer has been switched off, the monocarboxylic acids prepared by the process of the invention separate from the reaction mixture as liquid or powdery granular layers, depending on the reaction temperature, which float at the top and, in the case of the liquid layer, solidify to a solid plate on cooling. To remove inclosed chromic salts, the acids separated from the "chromium lye" are stirred repeatedly with dilute sulfuric acid at a temperature of from 90° to 100° C. This procedure is repeated until no chromic salts can be detected in the mineral acid. The acids are then washed with water at 90° to 100° C until all sulfuric acid has been removed.

The fatty acids or wax acids are obtained in amounts corresponding to 90 to 95% of the original alpha-olefin weight. They are absolutely colorless and very thermostable and, in view of these properties, they are very suitable for the manufacture of waxy esters and partial esters which can be used, for example, for making floor polishes and other polishes and for the manufacture of metal soaps, which can be used for example as drying substances or lubricants for plastic materials.

The following examples illustrate the invention

EXAMPLE 1

In an apparatus provided with stirrer, reflux condenser and and thermometer, 347 grams of a mixture of alpha-olefins having a chain length of 24 to 48 carbon atoms and an iodine number of 48.6, were oxidized at 110° to 112° C with 6,280 milliliters of chromosulfuric acid (106 grams $CrO_3$ and 540 grams $H_2SO_4$ per liter). After a reaction period of 6 hours, 98% of the chromic acid was consumed. From the cooled reaction mixture the waxy carboxylic acids formed could be isolated as solid plate floating on the aqueous phase. The adhering chromic compounds were removed by washing with dilute sulfuric acid at 100° C.

The wax acids were then treated with distilled water at boiling temperature until the washwater had a neutral reaction. After drying the colorless hard wax acids had the following characteristics:

Acid number 112, saponification number 129, iodine number 6, hydroxyl number 1, flow point/ drop point 88° to 89° C (according to Ubbelohde).

Yield: 330 grams, carboxylic acid content 70.5%.

EXAMPLE 2

107 Grams of a mixture of alpha-olefins having a chain length of 22 to 28 carbon atoms and an iodine number of 61 were oxidized as described in Example 1 with 1,990 milliliters of chromosulfuric acid (100 grams $CrO_3$ and 560 grams $H_2SO_4$ per liter). The colorless wax acids obtained after working up had the following characteristics:

Acid number 122, saponification number 123, iodine number 8, hydroxyl number 2, flow point / drop point 72 to 73° C.

Yield: 98 grams.

EXAMPLE 3

252 Grams of eicosene(1) were oxidized at 95° C as described in Example 1, with 4,260 milliliters of chromosulfuric acid (106 grams $CrO_3$ and 530 grams $H_2SO_4$ per liter) and the reaction mixture was worked up. The colorless carboxylic acid obtained had the following characteristics:

Acid number 131, saponification number 136, flow point/ drop point 55° to 56° C.

Yield: 225 grams

EXAMPLE 4

The α-olefin mixture as used in Example 1 was oxidized under the conditions in said example in a manner such that first 3,140 milliliters were allowed to act on the mixture, the oxidation agent which had been consumed after about 3 hours was separated and the oxidation was terminated with the other 3,140 milliliters of chromosulfuric acid, whereupon the mixture was worked up as specified in Example 1. The colorless wax acid mixture obtained contained 83.5% of carboxylic acid. The acid number was found to be 144 and the yield was 340 grams.

What we claim is:

1. Process for the manufacture of high molecular weight, aliphatic monocarboxylic acids by oxidizing alpha-olefins with a yield of from 90 to 95% by weight of the alpha-olefin employed, which consists essentially of treating straight-chained alpha-olefins having 16 to 70 carbon atoms in the molecule or mixtures of such alpha-olefins in the liquid state, without addition of any other substances or solvents at a temperature of from 100° to 115° C with aqueous chromosulfuric acid containing per liter 300 to 650 grams sulfuric acid and 50 to 140 grams chromium trioxide, the chromosulfuric acid being used in an amount such that 10 to 40 moles of chromium trioxide are present per 3 moles of alpha-olefin to be oxidized.

2. The process of claim 1, wherein the oxidation is carried out in two stages, in the first stage the olefins are reacted with at least 50% of the required amount of chromosulfuric acid, the consumed oxidation agent is separated and then the oxidation is terminated with the remainder of chromosulfuric acid.

* * * * *